United States Patent [19]

Brunelle

[11] 4,247,730

[45] Jan. 27, 1981

[54] HYDRODEALKYLATION OF ALKYLAROMATIC HYDROCARBONS

[75] Inventor: Jean-Pierre Brunelle, Fresnes, France

[73] Assignee: Procatalyse, Rueil Malmaison, France

[21] Appl. No.: 39,136

[22] Filed: May 15, 1979

Related U.S. Application Data

[63] Continuation of Ser. No. 840,635, Oct. 11, 1977, abandoned.

[30] Foreign Application Priority Data

Oct. 11, 1976 [FR] France .............................. 76 30533

[51] Int. Cl.$^3$ ................................................ C07C 4/12
[52] U.S. Cl. .................................... 585/489; 585/485; 585/486; 585/488
[58] Field of Search ................. 585/485, 486, 488, 489

[56] References Cited

U.S. PATENT DOCUMENTS

| | | | |
|---|---|---|---|
| 3,459,657 | 8/1969 | Kronig et al. ........................ | 585/269 |
| 3,595,932 | 7/1971 | Maslyansky et al. ................. | 585/487 |
| 3,597,348 | 8/1971 | Bourne et al. ....................... | 585/486 |
| 3,812,196 | 5/1974 | Uchiyama et al. ................... | 585/487 |

Primary Examiner—Curtis R. Davis
Attorney, Agent, or Firm—Burns, Doane, Swecker & Mathis

[57] ABSTRACT

A process for hydrodealkylating alkyl-substituted aromatic hydrocarbons, e.g., toluene, by reaction with hydrogen in the absence of water vapor under relatively mild reaction conditions, and a catalyst therefor are disclosed. The process is effected at a temperature of from about 450° to 650° C., preferably from about 520° to 620° C., and pressures of from about 1 to about 30, preferably from about 5 to about 20 bar, and a liquid hourly space velocity of from about 1 to about 10, preferably from about 3 to about 8, in the presence of a catalyst which comprises a noble metal component comprising rhodium and a support comprising a metal aluminate having a spinel structure and corresponding to the empirical formula M Al$_2$O$_4$.X Al$_2$O$_3$, wherein X represents a value of from 0 to about 200 and M represents a metal selected from the group consisting of nickel, cobalt, copper, zinc, iron, and magnesium.

Preferably, the support comprises an active alumina bearing a surface layer of said aluminate.

43 Claims, No Drawings

HYDRODEALKYLATION OF ALKYLAROMATIC HYDROCARBONS

This is a continuation of Application Ser. No. 840,635, filed Oct. 11, 1977, and now abandoned.

BACKGROUND OF THE INVENTION

1. Field of the Invention

The present invention to a process for hydrodealkylating alkyl-substituted aromatic hydrocarbons in the presence of a catalyst comprising rhodium and a support including a particular type of aluminate.

2. Description of the Prior Art

Two types of processes for hydrodealkylating alkyl-substituted aromatic hydrocarbons in a hydrogen atmosphere are presently known. These are thermal processes and catalytic processes.

The first type, which comprises a thermal hydrodealkylating reaction in the absence of any catalyst, has the important disadvantage of requiring very high reaction temperatures and pressures.

For the second type, it is recommended to use catalyst which comprise chromium oxide or a Group VIII metal.

The catalytic processes which are carried out in the presence of a catalyst comprising chromium oxide, such as described in the U.S. Pat. No. 2,858,348, usually requires lower reaction temperatures then those used in thermal processes. Yet, the same reflect the disadvantage of requiring a still too high hydrogen pressure and the catalyst lacks stability; therefore, such processes are only of little interest in actual practice.

Thus, the U.S. Pat. No. 2,734,929, discloses the use of a catalyst comprising an alumina support and, as an active component, the combination of a metal of Group VIB and a metal of Group VIII, preferably molybdenum or cobalt.

The U.S. Pat. No. 3,306,944, discloses a hydrodealkylation catalyst comprising an alumina support and, as an active component, rhodium, ruthenium, osmium or iridium.

The U.S. Pat. Nos. 3,686,340 and 3,825,503, disclose a hydrodealkylation catalyst comprising an alumina support and, as an active component, a composition including three components comprising a noble metal of Group VIII or nickel, tin oxide or lead oxide, an alkali metal or oxide or an oxide of an alkaline earth metal or a rare earth metal.

The U.S. Pat. No. 3,204,006, discloses a hydrodealkylation catalyst comprising a single noble metal of Group VIII, preferably platinum on alumina.

The U.S. Pat. No. 3,213,153, discloses a catalyst for hydrodealkylating alkyl naphthalenes which comprises, as an active component, a combination of a metal of Group VIII and a metal of Group VIA.

These prior art hydrodealkylation processes which use various catalytic formulations based on rhodium have major disadvantages. On the one hand, relatively elevated temperatures and pressures are needed for conducting same; on the other hand, they exhibit poor selectivity.

Furthermore, the stability of these catalytic formulations is usually low.

SUMMARY OF THE INVENTION

It is an object of the present invention to provide a hydrodealkylation process for alkylated aromatic hydrocarbons, which avoids these disadvantages attendant the state of the art.

It is a further object of the present invention to provide such a process which can be operated at significantly lower temperatures and pressure than those used in prior art catalytic hydrodealkylation processes.

It is a further object of the present invention to provide such a process which results in a high degree of reaction selectivity.

It is a further object to provide such a process, wherein a high degree of stability of the catalytic formulation is provided under the reaction conditions employed.

It is yet a further object of the present invention to provide a catalyst which catalyzes the hydrodealkylation of alkyl-substituted aromatic hydrocarbons at relatively mild reaction conditions, especially at relatively low temperatures and pressures.

It is still a further object of the present invention to provide such a catalyst which exhibits a high stability and which provides for a high reaction selectivity.

In order to accomplish the foregoing and other objects according to the present invention, there is provided a process for hydrodealkylating alkyl-substituted aromatic hydrocarbons, which comprises the step of reacting an alkyl-substituted aromatic hydrocarbon in the absence of water vapor with an amount of hydrogen sufficient to hydrodealkylate said alkyl-substituted aromatic hydrocarbon, in the presence of a catalyst which comprises a noble metal component comprising rhodium and a support comprising a metal aluminate having a spinel structure and corresponding to the empirical formula $M\ Al_2O_4 \cdot X\ Al_2O_3$, wherein X represents a value of from 0 to about 200 and M represents a metal selected from the group consisting of nickel, cobalt, copper, zinc, iron, and magnesium, at a reaction temperature and pressure and a liquid hourly space velocity sufficient to effect a hydrodealkylation of the alkyl-substituted aromatic hydrocarbon.

Preferably, the molar ratio between the alkyl-substituted aromatic hydrocarbon and the hydrogen is between about 1:10 and about 1:1. The reaction is preferably carried out at a temperature of between about 450° and about 650° C., and a pressure of between about 1 and about 30 bars.

The liquid hourly space velocity preferably is a space velocity of between about 1 to about 10 volumes of the liquid per volume of the catalyst, per hour.

According to a preferred embodiment of the present invention, the catalyst support may further comprise a conventional alumina-containing support which bears the above metal aluminate.

According to another embodiment of the present invention, the catalyst may further include a metal selected from the group consisting of platinum and palladium.

According to the present invention, there is further provided a catalyst for catalyzing the above hydrodealkylation, which comprises a noble metal component comprising rhodium and a support comprising a metal aluminate having a spinel structure, and corresponding to the empirical formula $M\ Al_2O_4 \cdot X\ Al_2O_3$, wherein X and M are as defined above.

Further objects, features and advantages of the present invention will become apparent from the following detailed description of the invention and its preferred embodiments.

DETAILED DESCRIPTION OF THE INVENTION

It has now been found that the above catalyst containing rhodium optionally in combination with platinum and/or palladium, and the particular aluminate support according to the present invention, catalyze the hydrodealkylation of alkyl-substituted aromatic hydrocarbons in a hydrogen atmosphere, in the absence of water vapor, under certain reaction conditions, namely, those of temperature and pressure, which are markedly milder than those used in the thermal or catalytic prior art processes, and provides for a very high degree of stability of the catalyst under these reaction conditions and a high degree of selectivity of the reaction.

One advantage of the present invention resides in the fact that the presence of rhodium and, optionally, platinum and/or palladium, deposited onto the particular aluminate support results in catalysts which are significantly more active, selective and stable vis-a-vis those disclosed in the prior art.

The catalyst support according to the present invention is entirely or partly comprised of aluminates of the following metals M: nickel, copper, iron, zinc, or magnesium.

The term "aluminate" according to the present invention is meant to connote the following:

A mixed oxide of aluminum and one of the above mentioned metals M having a spinel structure and corresponding to the empirical formula $M\ Al_2O_4 \cdot X\ Al_2O_3$, wherein X represents a value from 0 to about 200. If X equals zero, these aluminates correspond to the stoichiometric spinels. The non-stoichiometric spinels, wherein X represents a value of above zero, are derived from dissolving a corresponding amount of alumina, which may be a relatively high amount, in the cubic network of the stoichiometric aluminate spinel.

Solid solutions of at least two spinels in the case where at least two of the above cited metals M are used for preparing the catalyst support according to the present invention.

In a broader sense, the term "metal aluminate" according to the present invention also includes aluminates corresponding to the above empirical formula which are intermediate phases which are still poorly crystallized, yet, which lead to the formation of crystallized spinel compounds and wherein the oxides of the above cited metals are not in free form, yet have already entered a combination with the alumina.

In catalyst supports according to the present invention which are partly comprised by the above cited metal aluminates, the aluminate phase may be distributed homogeneously or heterogeneously throughout the interior of the entire support. In the latter case, it can be superficially fixed onto an already preformed support.

The support of the catalyst according to the present invention may be prepared in various manners, for example, the metal aluminates may be obtained from solid precursor compounds or mixtures of compounds which are prepared, e.g., by precipitating compounds which contain aluminum and the metal M, from solutions which contain soluble compounds of aluminum and/or the respective metal, hydrolyzing organo-metal compounds which contain aluminum and/or the metal M, crystallizing a precursor which contains aluminum and the metal M from a solution thereof by drying or lyophilization, or generally spoken, by any procedure which permits to obtain, simultaneously or successively, a bi- or multi-metal precursor which contains aluminum and the metal M and which leads to the formation of aluminate upon subsequent thermal treatment.

For this purpose, aluminum and at least one metal M selected from the group consisting of cobalt, iron, nickel, zinc, copper and magnesium are preferably used simultaneously in the form of an aqueous or an organic solution of inorganic or corresponding organo-metal precursors. Among commonly used precursors there may be cited the nitrates, chlorides, isopropylates, acetylacetonates and citric acid complexes of mineral salts and their sulfates.

The amounts of aluminum and the metals M are such that the ratio between the oxides $MO/Al_2O_3$ is between about 0.005 and about 1.

The bi- or multi-metal precursor which has been prepared according to one of the above cited methods or by any other known method is then dried and subsequently calcined by heating to an elevated temperature which may vary within a very large range, more particularly, within a range of between about 200° and about 1,200° C. The calcination may be effected in an oxidizing, an inert, or a reducing atmosphere.

A preferred process for preparing the support according to the present invention comprises preparing a catalyst support which comprises an alumina material which superficially bears the metal aluminate. Instead of alumina, alumina-containing compounds such as silica-alumina, and generally spoken, all mixed compounds of alumina which lead to the formation of aluminates, may also be used. According to an embodiment which is preferred because of the simple way of operation and the relatively low costs, the support according to the present invention is prepared by impregnating alumina particles with a solution of a precursor of the metal or metals which shall be deposited thereon. The metal(s) which are selected from the group consisting of iron, cobalt, nickel, copper, zinc, and magnesium lead to the formation of an aluminate on the surface of the alumina particles after drying and calcining. The term "surface" within this context does not designate the geometrical surfaces of the particles, but the internal surface which is accessible to the reactants and onto which the elements which have a hydrodealkylating activity are subsequently deposited.

The supports which comprise a surface layer of aluminate can be advantageously prepared according to the present invention starting from an active alumina which is obtained according to the process disclosed in the U.S. Pat. No. 2,915,365, the disclosure of which is hereby incorporated by reference and relied upon, or an active alumina which has been autoclaved in a neutral or aqueous acid medium and is obtained according to the process disclosed in the French Pat. Nos. 1,449,904 and 1,386,364, the disclosure of which is also hereby incorporated by reference and relied upon.

The process disclosed in the U.S. Pat. No. 2,915,365 comprises the transforming of hydrated alumina into an active alumina having a high absorption capacity, and includes the following steps:

(a) contacting the finely divided hydrated alumina with a stream of hot gas at a temperature between 400° and 1,000° C.;

(b) maintaining the contact between the hydrated alumina and the gas for a period of time of between a fraction of a second and 10 seconds; and, (c) separating the partially dehydrated alumina from the hot gases.

This alumina may have been agglomerated according to the process disclosed in the U.S. Pat. No. 2,881,051, the disclosure of which is also hereby incorporated by reference and relied upon.

According to the process disclosed in the French Pat. Nos. 1,449,904 and 1,386,364, the active alumina can be obtained by autoclaving the above described agglomerates of active alumina in an aqueous medium, optionally in the presence of an acid, at a temperature of above 100° C., preferably of between about 150° and about 250° C., during a period of time of preferably between about 1 and about 20 hours, and subsequently drying and calcining same. The calcination temperature is adjusted in such a way that a specific surface of preferably between about 100 and about 170 m²/g and a pore volume of preferably between about 0.5 and about 0.8 cm³/g are obtained. The resulting alumina has a gamma tetragonal crystallographical structure.

The amount of oxides of iron, cobalt, nickel, copper, zinc, and/or magnesium, which are deposited onto the support material, may vary depending on the specific metal oxide used and may comprise between about 0.1 and 80%, preferably from about 0.5 to about 5%, by weight, relative to the original support material. Any soluble inorganic or organo-metal compound containing the above metals M can be used for impregnating the support material. Yet, the most commonly used salts are the nitrates, chlorides, and sulfates of the metals M. The impregnated support material is then dried and calcined by heating it to a temperature of between about 200° and about 1,200° C., preferably between about 700° and about 1,000° C., in an inert, an oxidizing or a reducing medium. The calcining temperature has to be sufficiently high so that an aluminate is superficially formed as is defined before, and may vary considerably depending on the type and texture of the original support material, the type of the added metal oxide and the method of preparation. The calcining temperature should also not be too high in order to avoid destroying the texture of the original support material and obtaining an aluminate containing support the specific surface of which would be too small, which would be troublesome for achieving a good dispersion of the active hydrodealkylating elements.

The aluminate containing supports which are prepared according to the present invention preferably exhibit a specific surface of between about 50 and about 600 m²/g and a pore volume of between about 0.3 and about 1.0 cm³/g.

The catalysts according to the present invention comprise rhodium and optionally at least one further noble metal selected from the group consisting of platinum and palladium as active noble metals.

The rhodium, the platinum, and the palladium are deposited on the support in amounts of from about 0.05 to about 5%, preferably from about 0.1 to about 1%, by weight, relative to the support, whereby the per weight ratio between the amount of rhodium and the amount of the other two noble metals of Group VIII, which optionally are present, may vary within large limits, but preferably is between about 1:5 and about 5:1.

The catalyst can be prepared according to usual methods which comprise impregnating the support or carrier with solutions of inorganic or organic compounds of the metals which are intended to be deposited. The impregnation may be carried out with a solution containing all of the metals, or with different solutions, successively. As examples of soluble compounds of rhodium, platinum and palladium, the follow are exemplary: rhodium trichloride, chloroplatinic acid, palladium-II chloride, and the like. A homogeneous impregnation can be advantageously achieved by adding about 0.1 to about 10% of an inorganic or organic acid to the solution of the metal compounds. Usually, nitric acid, acetic acid or sulfuric acid are utilized.

After impregnating the support with any above solution, the catalyst is subsequently dried and then calcined in a stream of air at about 300° to about 800° C., for several hours.

Finally, the catalyst is reduced under a hydrogen atmosphere at a temperature of between about 300° to 650° C., for about 1 to 10 hours. The reduction of the catalyst can advantageously be carried out in the hydrodealkylation reactor. Reducing agents other than hydrogen too can be used.

The catalyst may advantageously be treated in an atmosphere containing a sulfur compound such as hydrogen sulfide. The sulfurizing step can be effected at any stage during the preparation of the catalyst.

The catalyst may be prepared in the form of spheres, extruded particles, pellets, or any other shape.

The hydrodealkylating reaction is effected in at least one reactor, whether drawing from fixed bed, mobile bed or fluidized bed techniques, and, optionally, providing for the alternative of regenerating the catalyst in a continuous or batch operation.

The reaction is effected at a temperature of between about 450° and about 650° C., preferably between about 520° and about 620° C.; the pressure is between about 1 and 30 bars, preferably between about 5 and about 20 bars.

The hourly space velocity is between about 1 and about 10, preferably between 3 and 8 volumes of liquid, per volume of catalyst, per hour. The molar ratio between the hydrogen and the alkyl-substituted aromatic hydrocarbons is between about 1 and about 10, preferably between about 3 and about 8.

The process according to the present invention is generally used for hydrodealkylating alkyl-substituted aromatic hydrocarbons. As alkyl-substituted aromatic hydrocarbons for which the process is especially suited, there may be mentioned benzene or naphthalene which are substituted by at least one lower alkyl group having from 1 to 5 carbon atoms, preferably a methyl group, for example, lower alkyl-substituted benzenes, such as, toluene and the xylenes.

The hydrodealkylating reaction may be effected upon a starting material containing either an above-mentioned aromatic hydrocarbon, in pure form, or upon a mixture of these hydrocarbons, optionally in the presence of other hydrocarbons such as paraffins.

Without limiting the present invention, the following examples are intended to further illustrate (1) the use of the rhodium containing combinations according to the present invention deposited on the particular supports described above, and, (2) their specific advantages as compared with catalysts wherein rhodium is deposited on a different alumina support, or with conventional prior art catalysts comprising chromium oxide.

EXAMPLE 1

The preparation of a catalyst (a) according to the present invention containing 0.5%, by weight, of rhodium deposited on a support consisting of stoichiometric magnesium aluminate is described in this example.

The support of stoichiometric magnesium aluminate was prepared as follows: a solution of aluminum isopropylate and magnesium acetyl acetonate in isopropanol containing 7%, by weight, of aluminum and 2.75%, by weight, of magnesium (corresponding to the stoichiometric ratio in the aluminate $MgO\text{-}Al_2O_3$) was introduced into an agitated autoclave and then hydrolyzed in the cold by adding an equivalent volume of an aqueous solution of isopropanol which contained an amount of water which was just sufficient to decompose the two organo-metal salts and form the hydroxides of the aluminum and the magnesium. The entire mixture was then heated in the autoclave to a temperature of 250° C. for several hours and was then subjected to a hypercritical drying at this temperature, whereby the pressure was released to normal atmospheric pressure.

By subjecting the resulting powder to an oxidizing treatment at a temperature of 600° C. for 3 hours, a finely crystallized magnesium aluminate was obtained, the crystalline structure of which was visible under X-ray irridiation, and the specific surface of which (determined according to the BET method) was 450 m$^2$/g, and the pore volume of which was 0.5 cm$^3$/g.

This crystalline aluminate powder was subsequently formed into pellets according to conventional methods and then was impregnated with a rhodium chloride solution.

The impregnation was effected by treating 100 g of said support material with 50 ml of an aqueous solution of rhodium trichloride containing 0.5 g of rhodium. After 3 hours of contact, the impregnated pellets were dried at 120° C. and then calcined under air at a temperature of 600° C. for 3 hours.

EXAMPLE 2

In this example, the preparation of two catalysts (B) and (C) according to the present invention comprising 0.5 or 1%, by weight, respectively, of rhodium deposited on a support of alumina balls the surface of which is made of copper aluminate is described.

Said support was prepared by impregnating 100 g of alumina which were obtained according to the process disclosed in U.S. Pat. No. 2,915,365, and which exhibited a specific surface of 250 m$^2$/g and a pore volume of 0.60 cm$^3$/g, with an aqueous solution of copper nitrate containing 4 g of the metal calculated as copper oxide. After several hours of contact, the impregnated alumina balls were dried at 120° C., then calcined under air at a temperature of 900° C. for 3 hours.

The data of the X-ray diffraction of the thus prepared support, indicated the presence of a spinel phase corresponding to a stoichiometric copper aluminate of the formula $CuAl_2O_4$ at the outsides of the alumina.

100 g each of the support are than impregnated with 60 ml of an aqueous solution containing either 0.5 or 0.1% of rhodium in the form of rhodium trichloride. After 3 hours of contact, the balls are dried at 120° C., and then calcined under air for 3 hours.

EXAMPLE 3

In this example, the procedure of Example 2 was repeated yet using as a starting support material alumina having a tetragonal structure. This particular alumina was prepared according to the French Pat. No. 1,449,904, by autoclaving agglomerates of active alumina in the presence of acetic acid and subsequent drying and calcination, and exhibited a specific surface of 120 m$^2$/g, a pore volume of 0.6 cm$^3$/g.

The resulting catalyst (D) contained 0.5%, by weight, of rhodium deposited on a support the surface of which was made of copper aluminate and was distinguished from the catalyst (B) only by the type of alumina which was used to prepare the catalyst support according to the present invention.

EXAMPLE 4

In this example, the procedure of Example 2 was repeated. Yet, impregnating the 100 g of active alumina which was obtained according to the method disclosed in the U.S. Pat. No. 2,915,365, by an aqueous solution of nickel nitrate, containing 4 g of the metal calculated as nickel oxide.

The data of the X-ray diffraction of the support which was obtained after impregnating, drying at 120° C. and then calcining at a temperature of 900° C. under air for 3 hours, indicated the presence of a non-stoichiometric nickel aluminate of spinel structure corresponding to the formula $2NiAl_2O_4.7Al_2O_3$.

By impregnating this nickel aluminate containing support with a solution of rhodium trichloride, a catalyst (E) according to the present invention containing 0.5%, by weight, of rhodium was obtained.

EXAMPLE 5

In this comparative example, the preparation of five catalysts (F), (G), (H), (I), and (J) are described which comprised only rhodium as an active element and wherein different alumina supports were used.

These supports corresponded to:
- an active alumina obtained according to the process described in the U.S. Pat. No. 2,915,365, for the catalysts (F) and (G).
- an active alumina prepared by treatment in an autoclave in the presence of acetic acid according to the process disclosed in the French Pat. No. 1,449,904, for the catalyst (H).
- an alumina of alpha structure exhibiting a specific surface of 70 m$^2$/g and a pore volume of 0.60 cm$^3$/g for the catalyst (I).
- an alumina of gamma cubic structure exhibiting a specific surface of 200 m$^2$/g and a pore volume of 0.55 cm$^3$/g for the catalyst (J).

The latter alumina is conventionally used as a catalyst support for catalysts for catalytic reforming processes.

The catalysts (F), (G), (H), (I), and (J) were prepared by impregnating the above cited supports each with 60 ml of a rhodium trichloride solution containing 0.5 g of rhodium in the form of rhodium trichloride for the catalysts (F), (H), (I), and (J), and 0.1 g of rhodium in the form of rhodium trichloride for the catalyst (G).

They are then dried at a temperature of 120° C. and calcined under air at a temperature of 600° C. for 3 hours.

In order to better evaluate the advantages which are achieved by using aluminate containing supports as supports for hydrodealkylation catalysts, on the one hand, the catalysts (A), (B), (D) and (E) according to the present invention were compared with the catalysts (F), (H), (I), and (J) and, on the other hand, the catalyst (C) according to the present invention was compared with the catalyst (G).

EXAMPLE 6

In this example, the preparation of five catalysts designated (K), (L), (M), (N), and (O) which demonstrate the use of bi-metal compositions of rhodium and palladium, which are, according to the present invention, deposited on a support the surface of which is comprised of an aluminate of either magnesium, cobalt, nickel, zinc, or iron.

The supports were prepared according to the following method: portions of 100 g of the active alumina described above in Example 2, each were impregnated with a solution of either magnesium nitrate, cobalt nitrate, nickel nitrate, zinc nitrate or iron nitrate in order to deposit thereon an amount of the salt corresponding to 4%, by weight, of the respective metal oxide. The material was allowed to ripen for several hours, then dried at 120° C., and then the cobalt-, nickel-, zinc-, or iron-containing supports were calcined at 800° C. for 3 hours, and the magnesium-containing support was calcined at 1,000° C. for 3 hours. 100 g of each of the thus prepared supports were subsequently impregnated with an aqueous solution of rhodium trichloride and palladium chloride containing 0.15 g of rhodium and 0.10 g of palladium. The resulting catalyst which was obtained after ripening, drying and calcining contained 0.15%, by weight, of rhodium and 0.10%, by weight, of palladium deposited on the support according to the present invention.

EXAMPLE 7

The bi-metal catalyst (P) which is described in this example, is given as a comparative catalyst for comparison with the catalysts (K), (L), (M), (N), and (O). It differs from the latter by the type of the support which was used, but not with regard to the active metal component, which also comprised 0.15%, by weight, of rhodium and 0.10%, by weight, of palladium. Yet, the support was an active alumina having a specific surface of 10 m$^2$/g and a pore volume of 0.60 cm$^3$/g.

The method which was used to prepare the catalyst, comprised impregnating the alumina with an aqueous solution of rhodium trichloride and palladium chloride, 3 hours of ripening, drying at 120° and calcining at 600° C. for 3 hours.

EXAMPLE 8

Here, for comparative purposes, a catalyst (Q) is described which contained 4%, by weight, of nickel oxide deposited on a silica support having a specific surface of 200 m$^2$/g, and a total pore volume of 1 cm$^3$/g.

The catalyst was prepared by impregnating the silica support with a solution of nickel nitrate, subsequently drying at 120° C. and calcining at 600° C. for 3 hours. After this thermal treatment, the nickel is present in free oxide form which is reducible under hydrogen at 600° C.

Its catalytic behavior which is described further below can be compared with that of the catalyst having a support the surface of which is nickel aluminate as described in Example 5, and wherein the nickel which is completely bound to the alumina of the starting support material after 3 hours of calcination at 800° C. exhibits no activity under the reaction conditions which are used in the text for hydrodealkylating toluene into benzene, which is described below.

EXAMPLE 9

The catalyst (R) which is described in this example, represents a conventional prior art catalytical formulation which gives good results only at more elevated reaction temperatures and pressures than those used in the process according to the present invention. This catalyst (R) contained 10%, by weight, of chromium oxide, Cr$_2$O$_3$, and was prepared by impregnating an alumina of a gamma cubic structure having a specific surface of 200 m$^2$/g and a pore volume of 0.55 cm$^3$/g with a solution of chromic acid. After impregnating, the catalyst is subjected to drying at 120° C. and then calcined under air for 3 hours.

The catalysts (A), (B), (C), (D), (E), (F), (G), (H), (I), (J), (K), (L), (M), (N), (O), (P), (Q), and (R), prepared according to the Examples 1-9, all were subsequently reduced under a hydrogen blanket at 550° C. for 2 hours, and then were tested in the absence of water vapor in a pilot plant assembly for hydrodealkylating toluene into benzene under the following reaction conditions:

Pressure: 10 bar
Temperature: 570° C.
Molar ratio hydrogen/toluene: 5
Liquid space velocity: 4 volumes of liquid per volume of catalyst per hour.

The conversions, selectivities and yields which were obtained after 3, 24 and 76 hours of continuous reaction, are given in Table I.

For simplifying purposes, in the Table I below, the active alumina support material which was obtained according to the process described in the U.S. Pat. No. 2,915,365, will be designated "flash alumina". In the same manner, the alumina having a gamma tetragonal structure which was prepared according to the process which is disclosed in the French Pat. No. 1,449,904 will be designated "autoclaved alumina".

The tests results which are given in the Table I below demonstrate the superior performance of the catalysts (A), (B), (C), (D), and (E) according to the present invention, as compared with that of the catalysts (F), (G), (H), (I), and (J). It is particularly apparent that in the reaction of hydrodealkylating toluene into benzene that catalysts which were prepared by depositing rhodium on a support the surface of which was comprised of a metal aluminate led to much superior yields than those which were obtained by depositing the same amount of rhodium on an alumina support.

In the same way, the comparison of the catalysts (K), (L), (M), (N), and (O) according to the present invention with the catalyst (P) leads to the same conclusions as above, with regard to bi-metal rhodium-palladium formulations using lower contents of noble metals.

Furthermore, under these test conditions, are noted, on the one hand, a relatively strong initial activity and a very poor selectivity of the catalyst (Q) wherein the nickel is not present in the form of an aluminate and, on the other hand, a very poor hydrodealkylating activity of the prior art catalyst (R) comprising chromium oxide.

TABLE I

| Example No. | Reaction period in hours | Conversion 3 | 24 | 76 | Selectivity 3 | 24 | 76 | Yield 3 | 24 | 76 |
|---|---|---|---|---|---|---|---|---|---|---|
| 1 | Catalyst (A) 0.5% Rh on Mg aluminate stoichiometrical | 83 | 75 | 72 | 96 | 98 | 98 | 80 | 73 | 70 |
| 2 | Catalyst (B) 0.5% Rh on Cu aluminate surface (ex.: flash alumina) | 77 | 86 | 83 | 97.5 | 95.5 | 94 | 75 | 82 | 78 |
| 2 | Catalyst (C) 0.1% Rh on Cu aluminate surface (ex.: flash alumina) | 27 | 40 | 41 | 98 | 99 | 98 | 26 | 40 | 40 |
| 3 | Catalyst (D) 0.5% Rh on Cu aluminate surface (ex.: autoclaved flash alumina) | 89 | 85 | 85 | 91 | 96 | 95 | 81 | 82 | 81 |
| 4 | Catalyst (E) 0.5% Rh on Ni aluminate surface (ex.: flash alumina) | 91 | 92 | 89 | 95 | 90 | 94 | 86 | 83 | 84 |
| Compara. 5 | Catalyst (F) 0.5% Rh on flash alumina | 19 | 66 | 61 | 93 | 85 | 85 | 18 | 56 | 52 |
| Compara. 5 | Catalyst (G) 0.1% Rh on flash alumina | 3 | 7 | 10 | 100 | 99 | 99 | 3 | 7 | 10 |
| Compara. 5 | Catalyst (H) 0.5% Rh on autoclaved flash alumina | 78 | 74 | 45 | 49 | 84 | 92 | 38 | 62 | 41 |
| Compara. 5 | Catalyst (I) 0.5% Rh on α-alumina | 69 | 53 | 12 | 39 | 35 | 96 | 27 | 18 | 11 |
| Compara. 5 | Catalyst (J) 0.5% Rh on $\gamma_c$-alumina | 63 | 66 | 57 | 37 | 30 | 29 | 23 | 20 | 16 |
| 6 | Catalyst (K) 0.15% Rh + 0.10% Pd on Mg aluminate surface (ex.: flash alumina) | 30 | 56 | 53 | 100 | 100 | 98 | 30 | 56 | 52 |
| 6 | Catalyst (L) 0.15% Rh + 0.10% Pd on Co aluminate surface (ex.: flash alumina) | 49 | 62 | 61 | 99 | 98 | 98 | 49 | 61 | 60 |
| 6 | Catalyst (M) 0.15% Rh + 0.10% Pd on Ni aluminate surface (ex.: flash alumina) | 50 | 56 | 50 | 98 | 99 | 98 | 49 | 56 | 49 |
| 6 | Catalyst (N) 0.15% Rh + 0.10% Pd on Zn aluminate surface (ex.: flash alumina) | 30 | 33 | 33 | 97 | 98 | 98 | 29 | 32 | 32 |
| 6 | Catalyst (O) 0.15% Rh + 0.10% Pd on Fe aluminate surface (ex.: flash alumina) | 37 | 53 | 56 | 99 | 99 | 99 | 37 | 53 | 56 |
| Compara. 7 | Catalyst (P)/0.15% Rh + 0.10% Pd on α-alumina | 32 | 24 | 4 | 41 | 54 | 98 | 13 | 13 | 44 |
| Compara. 8 | Catalyst (Q) 4% NiO on silica | 44 | 35 | 13 | 15 | 20 | 45 | 7 | 7 | 6 |
| Compara. 9 | Catalyst (R) 10% $Cr_2O_3$ on $\gamma_c$-alumina | 4 | 2 | 0.5 | 99 | 100 | 100 | 4 | 2 | 0.5 |

While the invention has now been described with reference to certain preferred embodiments, the skilled artisan will readily appreciate that various modifications, changes, substitutions, and omissions, may be made without departing from the spirit thereof. Accordingly, it is intended that the scope of the present invention be limited solely by that of the following claims.

What is claimed is:

1. A process for hydrodealkylating alkyl-substituted aromatic hydrocarbons, which comprises the step of reacting an alkyl-substituted aromatic hydrocarbon, in the absence of water vapor with an amount of hydrogen which is equivalent to a molar ratio between the alkyl-substituted aromatic hydrocarbon and the hydrogen of between about 1:10 to about 1:1, at a temperature of between about 450° and about 650° C., and under a pressure of about 1 to about 30 bars and a space velocity of between about 1 to about 10 volumes of the liquid per volume of the catalyst, per hour, in the presence of a catalyst which comprises a noble metal component comprising rhodium and a support comprising a metal aluminate having a spinel structure and corresponding to the empirical formula M $Al_2O_4$.X $Al_2O_3$, wherein X represents a value from 0 to about 200 and M represents a metal selected from the group consisting of nickel, cobalt, copper, zinc, iron and magnesium.

2. The process as defined in claim 1, wherein the noble metal component in the catalyst further comprises at least one additional noble metal selected from the group consisting of platinum and palladium.

3. The process as defined in claim 2, wherein the additional noble metal is palladium.

4. The process as defined in claim 2, wherein the ratio between the amount of said noble metal and the amount of rhodium is 1:5 to 5:1.

5. The process as defined in claim 1, wherein the amount of the noble metal component is from about 0.05 to about 5% by weight relative to the amount of the catalyst support.

6. The process as defined in claim 1, wherein the catalyst support has a specific surface of between about 50 and about 600 $m^2/g$.

7. The process as defined in claim 1, wherein the catalyst support has a pore volume of between about 0.3 and about 1.0 $cm^3/g$.

8. The process as defined in claim 1, wherein the catalyst support is essentially consisting of the metal aluminate.

9. The process as defined in claim 1, wherein the catalyst support comprises an alumina-containing support material bearing the metal aluminate.

10. The process as defined in claim 9, wherein the alumina-containing support material is selected from the group consisting of active alumina and mixed silicon and aluminum oxides.

11. The process as defined in claim 10, wherein the active alumina is obtained by dehydrating alumina hydrate in a stream of hot gas.

12. The process as defined in claim 11, wherein the dehydrating is effected at a temperature of between about 400° and about 1,000° C., and for a period of time of between a fraction of a second and about 10 seconds.

13. The process as defined in claim 10, wherein the active alumina comprises agglomerates of active alumina which have been autoclaved in an acid or neutral aqueous medium.

14. The process as defined in claim 13, wherein the active alumina has been autoclaved at a temperature of at least 100° C. for a period of time of from about 1 to about 20 hours, dried and calcined.

15. The process as defined in claim 1, wherein the support has been prepared by a process comprising the steps of:
(a) forming a precipitate containing an aluminum compound and at least one compound of a metal which is selected from the group consisting of nickel, cobalt, copper, zinc, iron, and magnesium;
(b) drying the precipitate; and,
(c) calcining at a temperature of between about 200° and about 1,200° C.

16. The process as defined in claim 15, wherein the precipitate forming step comprises precipitating water-insoluble compounds from an aqueous solution of a water-soluble aluminum compound and a water-soluble compound of the metal M.

17. The process as defined in claim 15, wherein the precipitate forming step comprises hydrolyzing an organo-metal compound containing aluminum and an organo-metal compound containing the metal M.

18. The process as defined in claim 15, wherein the precipitate forming step comprises crystallizing the aluminum compound and the compound containing the metal M from a solution thereof by means of drying.

19. The process as defined in claim 15, wherein the precipitate forming step comprises crystallizing the aluminum compound and the compound containing the metal M from a solution thereof by means of lyophilizing.

20. The process as defined in claim 15, wherein an aluminum-containing compound and a metal M containing compound selected from the group consisting of nitrates, chlorides, isopropylates, actylacetonates, and sulfates of aluminum and of the metal M, and citric acid complexes of their inorganic salts.

21. The process as defined in claim 15, wherein the aluminum compound and the compound of the metal M are present in such amounts which are equivalent to a molar ratio of the oxides $MO/Al_2O_3$ of between about 0.005 and about 1.

22. The process as defined in claim 15, wherein the calcining is effected in an oxidizing atmosphere.

23. The process as defined in claim 15, wherein the calcining step is effected in an inert atmosphere.

24. The process as defined in claim 15, wherein the calcining step is effected in a reducing atmosphere.

25. The process as defined in claim 15, wherein the calcining step is effected at a temperature of between about 700° and about 1,000° C.

26. The process as defined in claim 1, wherein the catalyst is prepared by a process comprising the step of impregnating the support with a solution of a rhodium compound.

27. The process as defined in claim 26, wherein the rhodium compound is an inorganic rhodium compound.

28. The process as defined in claim 26, wherein the rhodium compound is an organic rhodium compound.

29. The process as defined in claim 2, wherein the catalyst is prepared by a process comprising the step of impregnating the support with at least one solution of noble metal compounds comprising a rhodium compound and at least one compound of an additional noble metal selected from the group consisting of palladium and platinum.

30. The process as defined in claim 29, wherein the noble metal compounds are inorganic noble metal compounds.

31. The process as defined in claim 29, wherein the noble metal compounds are organic noble metal compounds.

32. The process as defined in claim 29, wherein the additional noble metal is platinum.

33. The process as defined in claim 29, wherein the additional noble metal is palladium.

34. The process as defined in claim 29, wherein the additional noble metal is a mixture of platinum and palladium.

35. The process as defined in claim 29, wherein the impregnating is effected with one common solution of the noble metal compounds.

36. The process as defined in claim 29, wherein the impregnating is effected by successive impregnation with separate solutions of each of the noble metals.

37. The process as defined in claim 20, wherein an amount of from about 0.1 to about 10% of an acid selected from the group consisting of nitric acid, acetic acid and sulfuric acid is added to the impregnating solution.

38. The process as defined in claim 29, wherein an amount of from about 0.1 to about 10% of an acid selected from the group consisting of nitric acid, acetic acid and sulfuric acid is added to the impregnating solution.

39. The process as defined in claim 26, which further comprises the steps of drying the catalyst, of calcining the dried catalyst in a stream of hot air at a temperature of between about 300° and about 800° C. for several hours to obtain a calcined product and of reducing the calcined product under hydrogen atmosphere at a temperature of between about 300° and about 650° C. for a period of time of between about 1 and about 10 hours.

40. The process as defined in claim 39, which further comprises treating the catalyst in an atmosphere containing a sulfur compound.

41. The process as defined in claim 29, which further comprises the steps of drying the catalyst, of calcining the dried catalyst in a stream of hot air at a temperature of between about 300° and about 800° C. for several hours to obtain a calcined product and of reducing the calcined product under hydrogen atmosphere at a temperature of between about 300° and about 650° C. for a period of time of between about 1 and about 10 hours.

42. The process as defined in claim 41, which further comprises treating the catalyst in an atmosphere containing a sulfur compound.

43. The process as defined in claim 1, wherein the alkyl-substituted aromatic hydrocarbon is a monocyclic aromatic hydrocarbon.

* * * * *